US012728200B2

(12) United States Patent
Fridez et al.

(10) Patent No.: US 12,728,200 B2
(45) Date of Patent: Sep. 8, 2026

(54) INSULIN PATCH PUMP HAVING PHOTOPLETHYSMOGRAPHY MODULE

(71) Applicant: Tandem Diabetes Care Switzerland Sàrl, St-Sulpice (CH)

(72) Inventors: Pierre Fridez, Froideville (CH); Laurent Mosimann, Commugny (CH); Antoine Barraud, Lonay (CH)

(73) Assignee: Tandem Diabetes Care Switzerland Sàrl, St-Sulpice (CH)

( * ) Notice: Subject to any disclaimer, the term of this patent is extended or adjusted under 35 U.S.C. 154(b) by 656 days.

(21) Appl. No.: 18/253,854

(22) PCT Filed: Nov. 19, 2021

(86) PCT No.: PCT/IB2021/060766
§ 371 (c)(1),
(2) Date: May 22, 2023

(87) PCT Pub. No.: WO2022/107078
PCT Pub. Date: May 27, 2022

(65) Prior Publication Data

US 2024/0001029 A1 Jan. 4, 2024

Related U.S. Application Data

(63) Continuation of application No. 17/102,334, filed on Nov. 23, 2020, now Pat. No. 11,241,530.

(51) Int. Cl.

| | |
|---|---|
| ***A61M 5/142*** | (2006.01) |
| ***A61B 5/024*** | (2006.01) |
| ***A61M 5/172*** | (2006.01) |

(52) U.S. Cl.
CPC ..... *A61M 5/14248* (2013.01); *A61B 5/02416* (2013.01); *A61M 5/1723* (2013.01);
(Continued)

(58) Field of Classification Search
CPC ............ A61M 5/14248; A61M 5/1723; A61M 2005/14208; A61M 2005/14252;
(Continued)

(56) References Cited

U.S. PATENT DOCUMENTS

| | | | |
|---|---|---|---|
| 2,105,200 | A | 1/1938 | Phelps |
| 2,412,397 | A | 12/1946 | Harper |

(Continued)

FOREIGN PATENT DOCUMENTS

| | | | |
|---|---|---|---|
| DE | 102013111800 | A1 | 4/2015 |
| EP | 1410814 | A2 | 4/2004 |

(Continued)

OTHER PUBLICATIONS

Accu-Check Solo, User's Manual, Accu-Check Solo micropump system, Roche Diabetes Care (2019).

(Continued)

*Primary Examiner* — James D Ponton
(74) *Attorney, Agent, or Firm* — Merchant & Gould P.C.

(57) ABSTRACT

A body-worn medication delivery pump having a patch form factor is provided that includes a controller and an integrated plethysmographic module that employs a photoplethysmographic multi-chip package disposed in a skin contact element designed to maintain contact with a wearer's skin during motion, reduce contact pressure inflammation during prolonged contact, reduce crosstalk and ingress of stray light, such that the controller of the pump programmed is programmed to adjust its medication delivery algorithms responsive to outputs of the plethysmographic module.

20 Claims, 6 Drawing Sheets

(52) U.S. Cl.
CPC ............ *A61M 2005/14208* (2013.01); *A61M 2005/14252* (2013.01); *A61M 2205/3327* (2013.01); *A61M 2205/583* (2013.01); *A61M 2205/587* (2013.01)

(58) Field of Classification Search
CPC .... A61M 2205/3327; A61M 2205/583; A61M 2205/587; A61M 5/16809; A61M 2005/14268; A61M 2205/13; A61M 2205/3303; A61B 5/02416; A61B 5/14532; A61B 5/4839; A61B 5/002
See application file for complete search history.

(56) References Cited

U.S. PATENT DOCUMENTS 3,609,069 A 9/1971 Martinelli
4,042,153 A 8/1977 Callahan et al.
4,199,307 A 4/1980 Jassawalla
4,218,416 A 8/1980 Gokcen
4,236,880 A 12/1980 Archibald
4,273,121 A 6/1981 Jassawalla
4,290,346 A 9/1981 Bujan
4,322,201 A 3/1982 Archibald
4,410,322 A 10/1983 Archibald
4,482,347 A 11/1984 Borsanyi
4,493,704 A 1/1985 Beard et al.
4,501,405 A 2/1985 Usry
4,596,575 A 6/1986 Rosenberg et al.
4,616,802 A 10/1986 Tseng et al.
4,617,014 A 10/1986 Cannon et al.
4,657,490 A 4/1987 Abbott
4,854,836 A 8/1989 Borsanyi
4,934,372 A 6/1990 Corenman et al.
5,056,992 A 10/1991 Simons et al.
5,066,278 A 11/1991 Hirschberg et al.
5,088,522 A 2/1992 Rath et al.
5,137,023 A 8/1992 Mendelson et al.
5,217,355 A 6/1993 Hyman et al.
5,252,044 A 10/1993 Raines et al.
5,318,546 A 6/1994 Bierman
5,482,446 A 1/1996 Williamson et al.
5,637,095 A 6/1997 Nason et al.
5,851,197 A 12/1998 Marano et al.
5,964,583 A 10/1999 Danby
6,093,172 A 7/2000 Funderburk et al.
6,165,151 A 12/2000 Weiner
6,293,925 B1 9/2001 Safabash et al.
6,607,509 B2 8/2003 Bobroff et al.
6,723,077 B2 4/2004 Pickup et al.
6,801,420 B2 10/2004 Talbot et al.
6,830,562 B2 12/2004 Mogensen et al.
6,881,043 B2 4/2005 Barak
7,137,964 B2 11/2006 Flaherty
7,204,823 B2 4/2007 Estes et al.
7,315,753 B2 1/2008 Baker, Jr. et al.
7,329,239 B2 2/2008 Safabash et al.
7,356,364 B1 4/2008 Bullock et al.
7,879,023 B2 2/2011 Wood, Jr.
7,879,026 B2 2/2011 Estes et al.
8,152,771 B2 4/2012 Mogensen et al.
8,377,002 B2 2/2013 Hanson et al.
8,657,807 B2 2/2014 Blomquist
9,114,208 B2 8/2015 Smith et al.
9,517,024 B2 12/2016 Kiani et al.
9,610,018 B2 4/2017 Gulati et al.
9,615,779 B2 4/2017 Pryor et al.
9,636,457 B2 5/2017 Newberry et al.
9,735,502 B2 8/2017 Stevens et al.
9,735,893 B1 8/2017 Aleksov et al.
9,820,691 B2 11/2017 Kiani
9,833,152 B2 12/2017 Kiani et al.
9,931,065 B2 4/2018 Pryor et al.
9,967,040 B2 5/2018 Aleksov et al.
9,980,140 B1 5/2018 Spencer et al.
9,993,595 B2 6/2018 Michaud et al.
10,137,245 B2 11/2018 Melker et al.
10,278,732 B2 5/2019 Schoonmaker et al.
10,279,106 B1 5/2019 Cook et al.
10,398,320 B2 9/2019 Kiani et al.
10,518,069 B2 12/2019 Boden, Jr. et al.
11,139,754 B1 10/2021 Shi et al.
11,241,530 B1 2/2022 Fridez et al.
11,529,460 B1 12/2022 Pruijs et al.
2002/0001530 A1 1/2002 Doi et al.
2002/0071225 A1 6/2002 Sheldon et al.
2002/0091358 A1 7/2002 Klitmose
2002/0169439 A1 11/2002 Flaherty
2004/0064088 A1 4/2004 Gorman et al.
2004/0082920 A1 4/2004 Mori et al.
2004/0158207 A1 8/2004 Hunn et al.
2005/0043687 A1 2/2005 Mogensen et al.
2005/0101912 A1 5/2005 Faust et al.
2005/0124936 A1 6/2005 Mogensen et al.
2005/0277887 A1 12/2005 Douglas et al.
2006/0036214 A1 2/2006 Mogensen et al.
2007/0060874 A1 3/2007 Nesbitt et al.
2007/0191772 A1 8/2007 Wojcik
2007/0191773 A1 8/2007 Wojcik
2007/0219496 A1 9/2007 Kamen et al.
2008/0051727 A1 2/2008 Moberg et al.
2008/0091175 A1 4/2008 Frikart et al.
2008/0097289 A1 4/2008 Steil et al.
2008/0281290 A1 11/2008 Yodfat et al.
2008/0319414 A1 12/2008 Yodfat et al.
2009/0069750 A1 3/2009 Schraga
2009/0118667 A1 5/2009 Haueter et al.
2009/0177146 A1 7/2009 Nesbitt et al.
2010/0004598 A1 1/2010 Eberhart et al.
2010/0017141 A1 1/2010 Campbell et al.
2010/0064236 A1 3/2010 Buck et al.
2010/0064257 A1 3/2010 Buck et al.
2010/0077198 A1 3/2010 Buck et al.
2010/0082167 A1 4/2010 Haueter et al.
2010/0106082 A1 4/2010 Zhou
2010/0174239 A1 7/2010 Yodfat et al.
2010/0211011 A1 8/2010 Haar
2010/0228226 A1 9/2010 Nielsen
2011/0054439 A1 3/2011 Yodfat et al.
2011/0137297 A1 6/2011 Kiani et al.
2011/0152769 A1 6/2011 Ramey et al.
2011/0218495 A1 9/2011 Remde
2011/0247397 A1 10/2011 Friedli et al.
2011/0266999 A1 11/2011 Yodfat et al.
2012/0051946 A1 3/2012 Lee et al.
2012/0059348 A1 3/2012 Haueter et al.
2012/0078181 A1 3/2012 Smith et al.
2012/0093311 A1 4/2012 Nierzwick et al.
2012/0093315 A1 4/2012 Nierzwick et al.
2012/0095393 A1 4/2012 Reinke et al.
2012/0150144 A1 6/2012 Campbell et al.
2012/0157655 A1 6/2012 Yoneda et al.
2012/0209187 A1 8/2012 Kamen et al.
2012/0220939 A1 8/2012 Yodfat et al.
2012/0226124 A1 9/2012 Blomquist
2012/0232485 A1 9/2012 Blomquist
2012/0232486 A1 9/2012 Blomquist
2012/0232521 A1 9/2012 Blomquist
2012/0239362 A1 9/2012 Blomquist
2012/0259185 A1 10/2012 Yodfat et al.
2012/0302991 A1 11/2012 Blomquist et al.
2013/0041342 A1 2/2013 Bernini et al.
2013/0060105 A1 3/2013 Shah et al.
2013/0079709 A1 3/2013 Eberhart et al.
2013/0245555 A1 9/2013 Dirac et al.
2013/0267811 A1 10/2013 Pryor et al.
2013/0338594 A1 12/2013 Da Ros et al.
2014/0128839 A1 5/2014 DiIanni et al.
2014/0148762 A1 5/2014 Haueter et al.
2014/0188516 A1 7/2014 Kamen et al.
2014/0249500 A1 9/2014 Estes
2014/0276419 A1 9/2014 Rosinko et al.
2014/0276420 A1 9/2014 Rosinko
2014/0276574 A1 9/2014 Saint

(56) References Cited

U.S. PATENT DOCUMENTS

2014/0288399 A1 9/2014 Regittnig
2014/0378898 A1 12/2014 Rosinko
2015/0073337 A1 3/2015 Saint et al.
2015/0182689 A1 7/2015 Dhami
2015/0182695 A1 7/2015 Rosinko
2015/0182697 A1 7/2015 Panzer
2015/0222517 A1 8/2015 McLaughlin et al.
2015/0265768 A1 9/2015 Vazquez et al.
2016/0008539 A1 1/2016 Miyazaki
2016/0030669 A1 2/2016 Harris et al.
2016/0067403 A1 3/2016 Moberg et al.
2016/0106910 A1 4/2016 Yap et al.
2016/0228641 A1 8/2016 Gescheit et al.
2016/0243302 A1 8/2016 Gyrn
2016/0254952 A1 9/2016 Harvey et al.
2016/0296715 A1 10/2016 Clemenz et al.
2016/0303333 A1 10/2016 Momose
2016/0339172 A1 11/2016 Michaud et al.
2017/0014572 A1* 1/2017 Newberry ........... A61M 5/1723
2017/0027523 A1 2/2017 Venkatraman et al.
2017/0056582 A1 3/2017 Niklaus
2017/0072140 A1 3/2017 Bazargan et al.
2017/0112534 A1 4/2017 Schoonmaker et al.
2017/0188911 A1 7/2017 Halac et al.
2017/0238805 A1 8/2017 Addison et al.
2017/0259015 A1 9/2017 Caspers
2017/0274146 A1 9/2017 Newberry et al.
2017/0368258 A1 12/2017 Fleischer
2018/0000999 A1 1/2018 Dolmatch et al.
2018/0025120 A1 1/2018 Cronrath et al.
2018/0060520 A1 3/2018 Degen et al.
2018/0207356 A1 7/2018 Joseph et al.
2018/0256813 A1 9/2018 Chow et al.
2018/0280608 A1 10/2018 Gillett et al.
2018/0318550 A1 11/2018 Chiu et al.
2018/0333532 A1 11/2018 Wei
2018/0339102 A1 11/2018 Barraud et al.
2019/0001055 A1 1/2019 Gyrn
2019/0083712 A1 3/2019 List
2019/0091404 A1 3/2019 Nazzaro et al.
2019/0133505 A1 5/2019 Jager
2019/0151568 A1 5/2019 Cardinali et al.
2019/0160225 A1 5/2019 Verlaak et al.
2019/0175818 A1 6/2019 Meenken
2019/0184072 A1 6/2019 Madden et al.
2019/0192768 A1 6/2019 Gupta et al.
2019/0255251 A1 8/2019 Diianni et al.
2019/0351134 A1 11/2019 Cook et al.
2020/0016335 A1 1/2020 DiPerna et al.
2020/0023122 A1 1/2020 McCullough et al.
2020/0037891 A1 2/2020 Kiani et al.
2020/0069875 A1 3/2020 Nazzaro et al.
2020/0101219 A1* 4/2020 Wang ................ A61M 5/14248
2020/0329433 A1 10/2020 Kruse et al.
2020/0360235 A1 11/2020 Møller
2020/0373009 A1 11/2020 Shapley et al.
2021/0038813 A1 2/2021 O'Connor et al.
2021/0093779 A1 4/2021 Trachtenberg
2021/0162119 A1 6/2021 Barraud et al.
2021/0213198 A1 7/2021 Gyory
2021/0272687 A1 9/2021 Klopfenstein et al.
2021/0280309 A1 9/2021 Klopfenstein et al.
2022/0226568 A1 7/2022 Oberg et al.

FOREIGN PATENT DOCUMENTS

EP 1716879 A1 11/2006
EP 1944150 A1 7/2008
EP 2698178 A2 2/2014
GB 2065789 A 7/1981
WO WO-8001934 A1 9/1980
WO WO-0220073 A2 3/2002
WO WO-2005016534 A1 2/2005
WO WO-2008155377 A1 12/2008
WO WO-2017085624 A1 5/2017
WO WO-2017205816 A1 11/2017
WO WO-2019110839 A1 6/2019

OTHER PUBLICATIONS

Medtronic MiniMed (tm) 770G, System User Guide, https://www.medtronicdiabetes.com/sites/default/files/library/download-library/user-guides/MiniMed_770G_System_User_Guide.pdf (2020).

Omnipod-Insulin Management System, UST400 User Guide, https://www.omnipo.com/sites/default/files/2021-04/Omnipod-System_User-Guide_English (Apr. 2021).

Osram—Light is Wearable, Health Monitoring and Fitness Tracking, Osram Opto Semiconductors, Flyer posted online Jan. 22, 2015, (Year: 2015).

T:slim Insulin Pump, User Guide, Tandem Diabetes Care, https://www.tandemdiabetes.com/docs/default-source/product-documents/tslim-insulin-pump (2017).

Examination Report of the European Patent Office, EP21816168.5, dated Oct. 30, 2025, 6 pages.

* cited by examiner

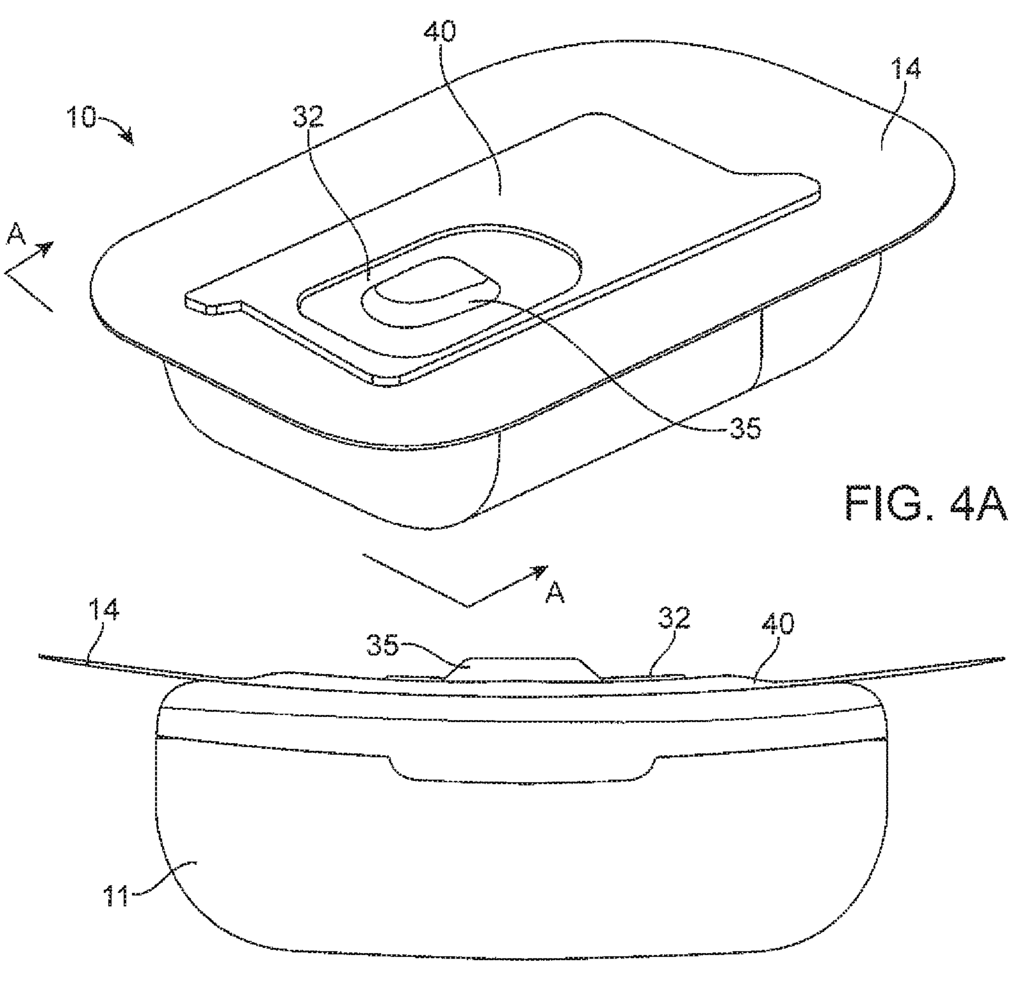
FIG. 4A
FIG. 4B
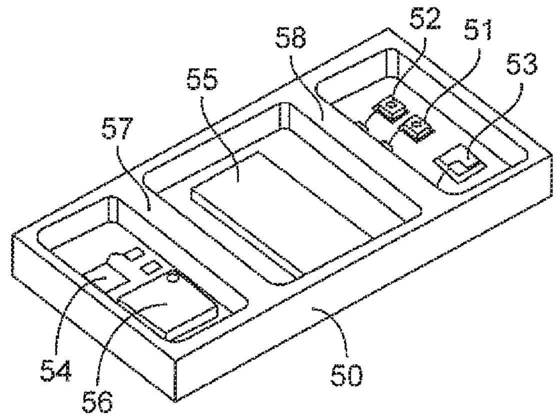
FIG. 5

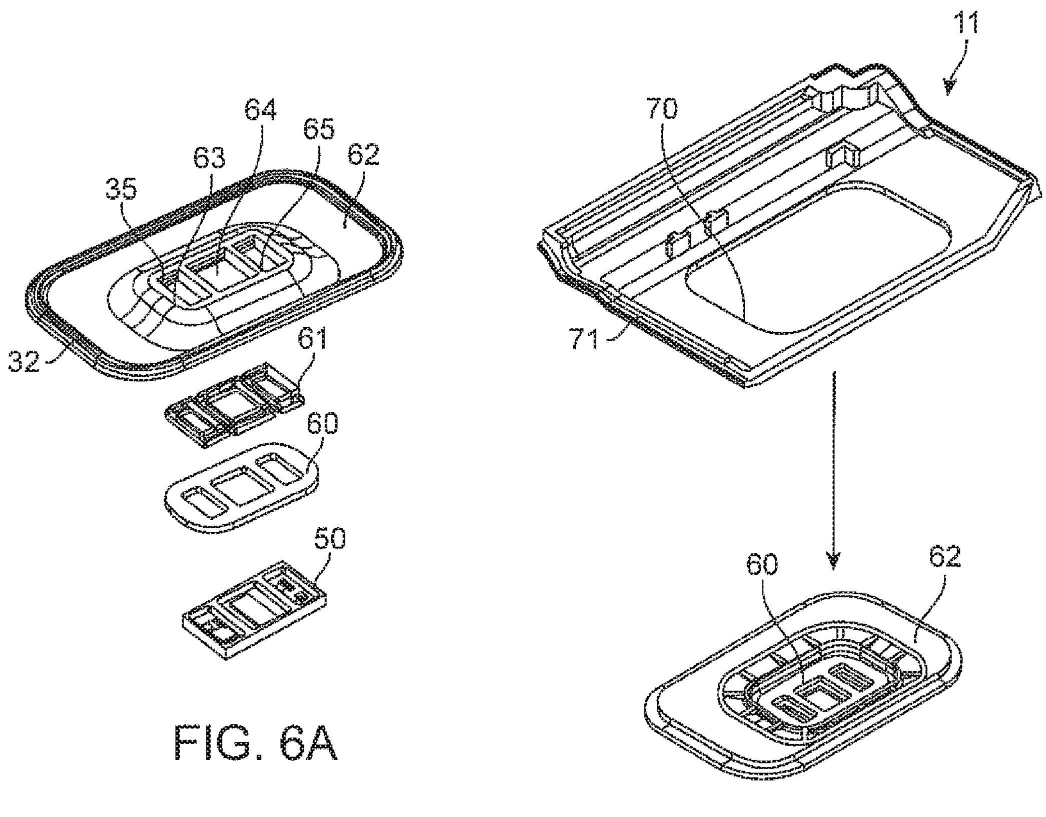
FIG. 6A
FIG. 7
50
60
62
32
35
61
63
64
65
FIG. 6B
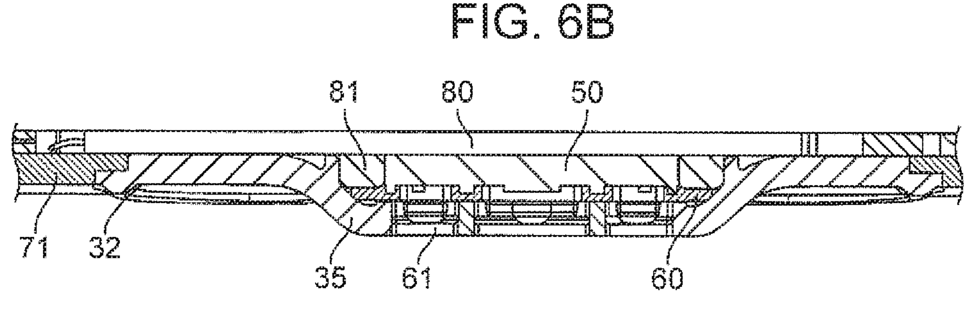
FIG. 8

INSULIN PATCH PUMP HAVING PHOTOPLETHYSMOGRAPHY MODULE

CROSS-REFERENCE TO RELATED APPLICATIONS

This application is a national phase application under 35 U.S.C. § 371 of PCT/IB2021/060766, filed Nov. 19, 2021, which claims priority to U.S. patent application Ser. No. 17/102,334, filed Nov. 23, 2020, now U.S. Pat. No. 11,241, 530, the entire contents of each of which are incorporated herein by reference.

I. FIELD OF THE INVENTION

This invention relates generally to the wearable insulin pumps having a patch-style form factor for adhesion to a user's body surface, and more particularly to an insulin patch pump having a photoplethysmography module for sensing a user's heart rate and/or other physiologic parameters.

II. BACKGROUND OF THE INVENTION

Wearable insulin pumps are known for providing a Type I Diabetes Mellitus patient with periodic bolus infusions of insulin to control the patient's blood glucose level within a desired range. Some such insulin pumps are coupled to an adhesive patch that permits the pump to be directly adhered to a user's body surface, for example the abdomen, and are referred to as "patch pumps." In addition, some previously known systems were configured to interface wirelessly with a continuous glucose monitor, which typically also may be disposed on a patch designed to be adhered to the user's body. Other previously known systems employ still further modules designed to monitor user activity and report that activity to a controller associated with the patch pump to titrate the insulin delivery in accordance with the user's activity level.

For example, U.S. Pat. No. 7,879,026 describes an infusion pump that is designed to be wearable, e.g., on a user's belt, and is coupled to an infusion cannula that extends through and is fixed to a user's skin using an adhesive patch. The infusion pump may include an accelerometer or other motion sensor to detect the user's activity level, the output of which may be used to automatically adjust a rate of dispensation of insulin to the user based at least in part on the detected movement activities of the user. The patent does not describe patch-based insulin pump nor use of a plethysmographic sensor to detect movement to control operation of such a pump.

U.S. Pat. No. 9,636,457 describes an integrated drug delivery and biosensor system that may be disposed on a patch or armband, wherein the biosensor monitors absorption of medication into the epidermis of the skin and also monitors concentration of the medication in the user's arterial blood flow. The patent describes that the biosensor system employ a photoplethysmography (PPG) circuit configured to obtain the concentration levels of medication in the user's arterial blood flow, as well as detect blood oxygen saturation, heart rate and blood pressure. That patent does not provide mechanical solutions to filter out the effects of cross-contamination of light impinging upon the PPG circuit detector element.

U.S. Pat. No. 9,735,893 describes a patch system for in-situ therapeutic treatment wherein a plurality of biological parameter monitoring devices may be disposed on separate stretchable patches designed to adhere to a user's skin. The monitoring devices communicate with each other, and other therapeutic devices, via short-range wireless, such as Bluetooth. The patent describes that patch-based monitoring devices may be configured to communicate to a belt-worn insulin pump, and that one patch-based monitoring device may include pulse oximetry electronics for measuring blood volume. The patent does not describe a patch-based insulin pump and requires intercommunication between its various components, providing a potential failure mode.

U.S. Patent Application Publication No. US 2018/0339102, assigned to the assignee of the instant application, describes a self-contained patch pump having a motor-actuated syringe together with a microdosing pump chamber. The infusion pump described in the application provides reliable and highly reproducible long-term drug infusion capability, but does not describe any on-board physiologic sensors.

U.S. Pat. No. 4,934,372 describes a standalone pulse oximeter that includes frequency domain software for determining blood oxygen saturation and heart rate in the presence of motion artifact. Similarly, U.S. Pat. No. 7,315,753 describes a method of determining heart rate and blood oxygen saturation in the presence of motion artifact, for use in standalone pulse oximeters, using Kalman filters.

In view of the foregoing drawbacks of previously known systems, there exists a need for a patch pump that includes self-contained circuitry for secondary factors that impact blood glucose level, such as physical activity determined by measuring heart rate, and which circuitry uses that indicator of physical activity to adjust dosing of insulin.

It further would be desirable to have an insulin delivery system with an integrated plethysmographic module that overcomes the drawbacks of previously known systems, and includes the ability to read through motion.

It further would be desirable to have an insulin delivery system with an integrated photo-plethysmographic module that is configured to reduce cross talk between the light emitting diodes and the detector of the module.

III. BRIEF DESCRIPTION OF THE DRAWINGS

FIGS. 4A and 4B are, respectively, a perspective view of the patient-facing side of the insulin delivery pump of the present invention with the adhesive patch present and an end view of the device.

FIG. 5 is a perspective view of a multi-chip package suitable for implementing the plethysmographic module of the integrated insulin delivery pump of the present invention.

FIGS. 6A and 6B are, respectively, an exploded perspective view and a side sectional view of the plethysmographic module of the present invention including the multi-chip package of FIG. 5.

FIG. 7 is a perspective view illustrating assembly of the plethysmographic module with the patient-facing surface of the exterior case of the insulin delivery pump of the present invention.

FIG. 8 is a side sectional view on the plethysmographic module assembled with the patient-facing surface of the exterior case of the insulin delivery pump.

IV. SUMMARY OF THE INVENTION

In view of the foregoing drawbacks of the previously known systems, the present invention is directed to an insulin delivery pump, in a patch form factor that can be applied to a user's body surface, and includes an integral plethysmographic module for determining physical activity. In accordance with one aspect of the invention, the plethysmographic module employs a photo-plethysmographic multi-chip package and is configured to maintain contact with the user's body surface during motion, and for extended periods, without causing skin abrasion, pressure sores, inflammation or tissue necrosis, while also reducing cross talk between the emitters and detectors and from ambient light impinging upon the plethysmographic module.

In one preferred embodiment, the multi-chip package is housed in a skin contact element that urges the plethysmographic module into contact with a skin surface of a torso of a wearer, such as the abdomen, with sufficient force to maintain skin contact during vigorous motion of the wearer. In one preferred embodiment, the skin contact element includes a frame disposed on an embossment projecting from a patient-facing surface of the pump case, including a protruding portion optionally surrounded by a light-blocking rib. The protruding portion extends above embossment on the patient-facing exterior of the insulin delivery pump case and extends through an opening in the adhesive patch. In this way the frame is urged against and maintains contact with the skin of the user's body surface even when the user is active, thereby reducing the introduction of motion artifact into the heart rate signal determined by the plethysmographic module.

In accordance with another aspect of the invention, the insulin delivery pump includes on-board controller for processing the signals generated by the plethysmographic module to determine a user's heart rate, and for adjusting delivery of insulin from the pump responsive to the measured heart rate. The software employed by the on-board controller for processing the signals generated by the plethysmographic module illustratively may employ a frequency domain analysis, for example, as described in U.S. Pat. No. 4,934,372, or Kalman filter approach, as described in U.S. Pat. No. 7,315,753, the entireties of which are incorporated herein by reference, to reduce the motion artifact in the photoplethysmographic signals.

V. DETAILED DESCRIPTION OF THE PREFERRED EMBODIMENTS

Figures 1, 2, 3:
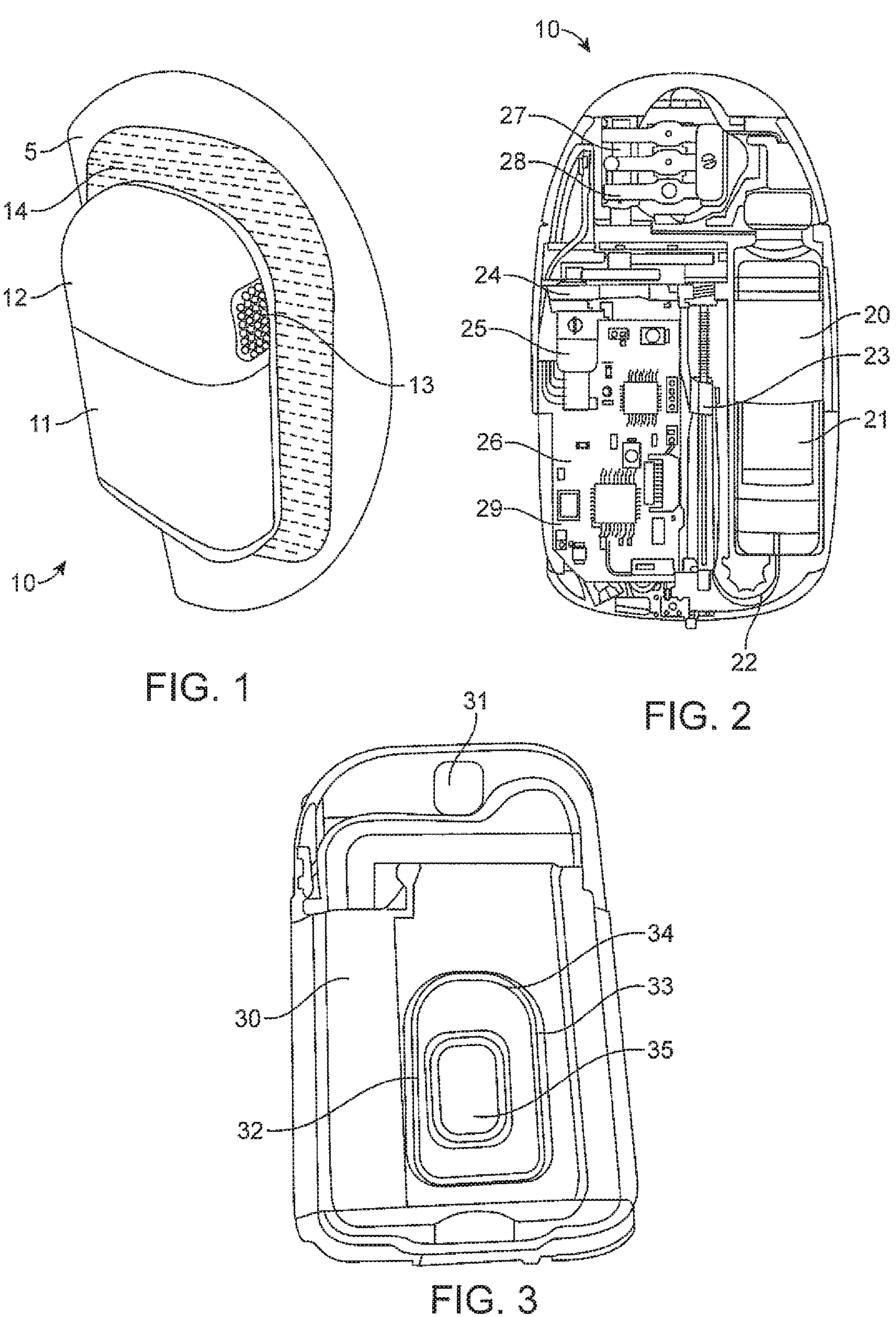
FIG. 1 is an illustrative perspective view of an insulin delivery patch pump having an integrated plethysmographic module, in accordance with the present invention, adhered to a body surface of a user.
FIG. 2 is an illustrative schematic depicting the interior of the insulin delivery pump of the embodiment of FIG. 1.
FIG. 3 is an illustrative perspective view of a prototype of the patient-facing side of the insulin delivery pump of the present invention, with the adhesive patch removed.
Figure 9:
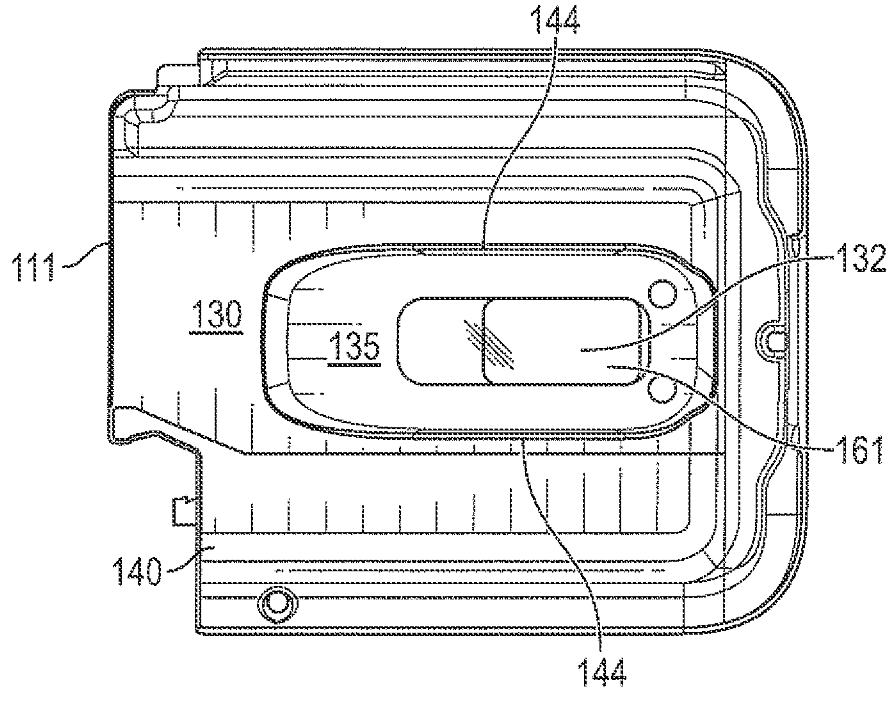
FIG. 9 is a plan view of the exterior patient-facing side of the pump portion of an alternative embodiment of the insulin delivery pump of the present invention.

Referring to FIG. 1, first exemplary patch pump 10 having integrated photoplethysmographic module constructed in accordance with the principles of the present invention is described. In this disclosure, exemplary patch pump 10 is configured to infuse measured amounts of insulin from an on-board reservoir into a user's subcutaneous tissue via transcutaneous needles. As depicted in FIG. 1, patch pump 10 illustratively includes exterior case 11 having removable cap 12 and button 13 that enables the user to removably attach the exterior case to breathable, preferably stretchable adhesive patch 14 that adheres to a user's body surface skin S, e.g., such as a wearer's arm or abdomen. Illustratively, patch pump 10 is configured to deliver insulin for treatment of Type I Diabetes Mellitus, although the inventive system advantageously could be employed to deliver other medications. Removable cap portion 12 contains drug delivery measurement components, preferably including a high accuracy micro-doing system. Exterior case 11 is separable from removable cap 12 and preferably houses a replaceable cartridge, the electromechanical components, and the plethysmographic module of patch pump 10, as further described below.

In accordance with one aspect of the invention, photoplethysmography is employed to determine heart rate as indicative of a wearer's physical activity, which physical activity level then is assessed to adjust the amount of insulin provided by patch pump 10. For example, using physical activity level, or a determination that the wearer is sleeping or awake, a small change may be made in an algorithm that controls an amount or rate of insulin injection, which could significantly influence blood glucose level. As described herein, the patch pump controller could use heart rate determined by the photoplethysmographic module to implement a sport mode, for example, that permits a slightly higher glucose target to decrease the risk of hypoglycemia after physical exertion.

FIG. 2 is a plan view of the internal components of patch pump 10 with an upper portion of exterior case 11 removed. Patch pump internal components preferably are arranged as described in commonly assigned U.S. Patent Application Publication No. US 2018/0339102, which is incorporated herein by reference. More specifically, patch pump 10 includes replaceable single-use cartridge 20 having plunger 21 coupled to actuator 22 and drive screw 23. Drive screw 23 is coupled to gear system 24 and is driven by battery-driven motor 25 under the control of controller 26. Gear system 24 also is coupled to micro-dosing unit 26, which is operated by three cam-driven levers 27. As described in the above-incorporated patent publication, medication ejected from reservoir 20 into microdosing unit 26 is infused into the user by sequential operation of levers 27. Doses of medication are delivered to the user responsive to operation of controller 26, in accordance with programming stored in memory associated with controller 26 or specifically when requested by the user, e.g., using a suitable wireless application on the user's smartphone. Controller 26 includes multiple electronic components affixed to main circuit board 28, including at least a processor, memory, wireless transceiver and battery. In accordance with the principles of the present invention, controller 26 also may include electronics for processing the output of a photoplethysmography module to determine a user's activity level, including heart rate, blood oxygen saturation, and other physiologic parameters, which may be processed to adjust the insulin delivery rate or amount to control the wearer's blood glucose level.

Referring to FIG. 3, an exemplary embodiment of patient-facing side 30 of first exterior case 11 of patch pump 10 is described. Patient-facing side 30 preferably is configured to be attached to the skin of a wearer's torso, such as the abdomen, and is adhered to adhesive patch 14. Patient-facing side 30 includes aperture 31 through which a transcutaneous infusion needle (not shown) exits exterior case 11. Side 30 includes optional raised light-blocking rib 32, having an approximately rectangular shape 33 with a semi-circular top 34, that mates with a similarly shaped opening in adhesive patch 14. Rib 32 surrounds protrusion or bump 35 that projects from side 30 above the height of rib 32. As detailed below, bump 35 houses the photoplethysmography module LEDs and detectors, and preferably is disposed on a raised or embossed surface of the exterior of the pump case. Rib 32, if present, is designed to reduce ambient light from impinging on the detectors of the photoplethysmography module, while bump 35 projects from side 30 of exterior case 11 a predetermined distance to ensure that photoplethysmography module remains in contact with the user's skin during body motion.

Referring now to FIGS. 4A and 4B, location of the photoplethysmography module of patch pump 10 relative to adhesive patch 14 is described. In particular, FIG. 4A is a perspective view of the patient-facing side of adhesive patch 14, showing embossment 40, optional raised rib 32, and bump 35, while FIG. 4B is an end view of patch pump 10 taken along view line A-A. As depicted in FIGS. 4A and 4B, patient-facing surface 30 of exterior case 11 also may include a slightly concave contour to better conform to the skin surface. Adhesive patch 14 affixed to side 30 includes a periphery that engages the exterior of case 11 and defines opening 41 through which the area encompassed by optional rib 32 protrudes from side 30 to contact a user's skin. Embossment 40 establishes a first plane above which light-blocking rib 32 extends to surround bump 35. Bump 35 extends above the surface of embossment 40 so that when adhesive patch 14 is applied to a user's body surface, the bump remains in continuous contact with a user's skin during motion. Bump 35 preferably protrudes above the surface of embossment 40 from about 0.6 mm to 2 mm, which height is selected to maintain contact of bump 35 with the user's skin while ensuring that the contact force of bump 35 does not apply excessive pressure to the skin or cause tissue necrosis.

FIG. 5 depicts illustrative multi-chip photoplethysmography package 50 suitable for use in the integrated patch pump of the present invention, for example, the SFH 7072 BIOFY® Sensor device available from OSRAM Opto Semiconductors GmbH, Regensburg, Germany. PPG package 50 is to generate a photoplethysmography signal suitable for heart rate monitoring and pulse oximetry, and includes red LED 51, infrared LED 52, green LEDs 53 and 54, infrared cut detector 55 to detect reflected light from green LEDs 53 and 54 and broadband detector 56 to detect reflected light from red LED 51 and infrared LED 52. In one preferred embodiment, the red LED has a centroid wavelength of 655 nm, the infrared LED has a centroid wavelength of 940 nm and the green LEDs have a centroid wavelength of 530 nm. The LEDs and detectors are set in a ceramic package that includes light barriers 57 and 58 to reduce optical crosstalk between the LEDs and detectors.

As is well known in the photoplethysmography art, green LEDs are commonly used in monitoring heart rate in wearables in view of their good signal-to-noise ratio and resistance to motion artifact, while the combination of red and infrared LEDs for accurately monitoring blood oxygen saturation. Suitable algorithms are known in the art for processing photoplethysmographic signals generated with red and infrared LEDs and green LEDs to reduce the effects of motion noise, including frequency domain analysis and Kalman filter analysis techniques. Alternatively, the infrared-red LEDs may be used, instead of the green LEDs, to compute heart rates for wearers having darker skin complexions. PPG package 50 of FIG. 5 is intended to be illustrative, and more or fewer LEDs advantageously could be employed in the plethysmographic module of the present invention.

In accordance with one aspect of the invention, PPG package 50 is assembled together with layer 60 and transparent window 61 into frame 62 which forms bump 35 of FIGS. 4A and 4B, as depicted in FIGS. 6A and 6B. Frame 62 preferably comprises a sturdy biocompatible plastic or rubber material that may be formed, e.g., by overmolding on window 61, to create integral rib 32 and bump 35 having openings 63, 64 and 65. Transparent window 61 may consist of a clear plastic or glass-like material having low absorptivity for light at the wavelengths of the LEDs of PPG package 50, and is designed to mate with the overmolded openings of frame 62 to provide a smooth exterior surface for bump 35. Layer 60 preferably is a closed cell foam or similar compressible material against which PPG package 50 is urged against layer 60 into contact with transparent window 61. Layer 60 and frame 62 preferably are matte gray or matte black to reduce light scattering of light reflected from tissue through window 61.

In FIG. 7, assembly of frame 62 together, layer 60 and window 61 with exterior case 11 of patch pump 10 is described. Once frame 62 is overmolded on window 61, layer 60 may be glued in place. That assembly then is mated with opening 70 in exterior wall 71 of exterior case 11, and laser welded around its perimeter to affix the frame within opening 70. PPG package 50, with its electrical components electrically coupled to printed circuit board 80, then is assembled, along with spacer 8, as depicted in FIG. 8. Spacer 81 retains PPG package 50 in alignment with window 61 in frame 62. Printed circuit board 80 preferably is electrically coupled to main circuit board 28 of controller 26, e.g., via a flex circuit, to provide signals that permit calculation of heart rate and/or blood oxygen saturation. Circuit board 80 or main circuit board 28 additionally may have an accelerometer to determine the orientation of the user's body, e.g., upright or supine, to assess whether the user is active, resting or asleep.

In accordance with the principles of the present invention, heart rate signals generated by the on-board plethysmography module are used by controller 26 to modulate infusion of insulin from patch pump 10. In a preferred embodiment, the plethysmography module periodically measures the wearer's heart rate, e.g., once every minute, 2½ minutes or five minutes, and computes a heart rate and a quality measure for the computed heart rate. The quality measure may be used to determine whether to adjust insulin delivery to better maintain the stability of the wearer's blood glucose level.

In addition, the heart rate data may be used to compute an activity intensity level, similar to that employed in physical activity monitors, such as resting, passive behavior, and low, medium and high levels. Such an activity level could be used to adjust parameters of the insult delivery algorithm to permit a "sport mode" that adjusts insulin delivery to reduce the risk of hypoglycemia during, and especially after, engaging in vigorous or sports activities. The heart rate also could be evaluated to determine whether the wearer is asleep or awake. For example, when a wearer is asleep, the parameters of the infusion algorithm used in controller 26 could be switched to a sleep mode. This sleep mode may allow fine-tuning of the wearer's glucose level to allow provide better sleep well and improve time in a targeted glucose range. Such adjustments are expected to be possible because while sleeping, the wearer does not eat, is not physically active and is not physically or emotionally stressed.

Determination that a wearer is asleep or awake additionally could be based on, or confirmed by, data from the on-board accelerometer discussed above. Accelerometer outputs also could be analyzed to assess where patch pump 10 is being worn by the user, and to determine body orientation. The sleep/wake information also may be analyzed to provide a quality measure of the measurement, and thus allow the infusion algorithm employed by the controller to have a good degree of confidence regarding its insulin delivery adjustments.

The output of the on-board plethysmographic module also may be used to validate that patch pump 10 is adequately adhered to the wearer's skin to allow insulin injection. If, for example, patch pump 10 includes a capacitive circuit for continuously detecting that the pump is adhered to a wearer's skin, the plethysmographic module could provide confirmation that the pump is located on the wearer's skin.

Referring now to FIGS. 9-15, an alternative embodiment of the patch pump of the present invention is described. With respect to FIG. 9, patient-facing side 130 of exterior case 111 of an alternative patch pump is described, and may be used with removable cap 12 of FIG. 1. Like the previous embodiment of FIGS. 1-8, patient-facing side 130 of this alternative embodiment preferably is configured to be attached to the skin of a wearer's torso, such as the abdomen, and is adhered to adhesive patch (not shown). Side 130 includes an approximately rectangular-shaped protrusion or bump 135 that projects from side 130 above embossed surface 140 of the exterior of pump case 111. Bump 135 houses photoplethysmography module 132 consisting of LEDs and detectors, and preferably projects from side 130 of exterior case 111 a predetermined distance to ensure that photoplethysmography module 132 remains in contact with the user's skin during body motion. Unlike the embodiment of FIG. 1, in which transparent window 61 included portions that cover specific regions of the photoplethysmography module LEDs and detectors, transparent window 161 of the embodiment of FIGS. 9-15 is flat and spans entire module 132.

Figure 10:
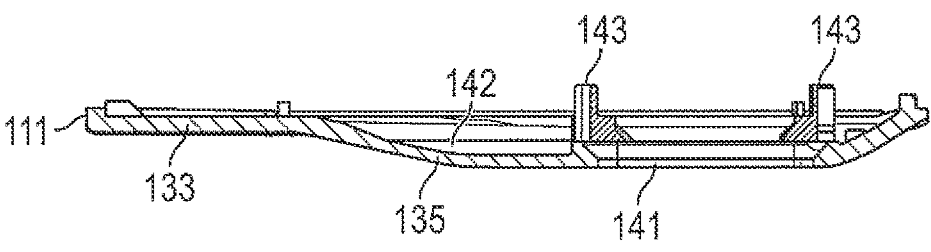
FIG. 10 is a side sectional view of the exterior pump case component of embodiment of FIG. 9.
Figure 11:
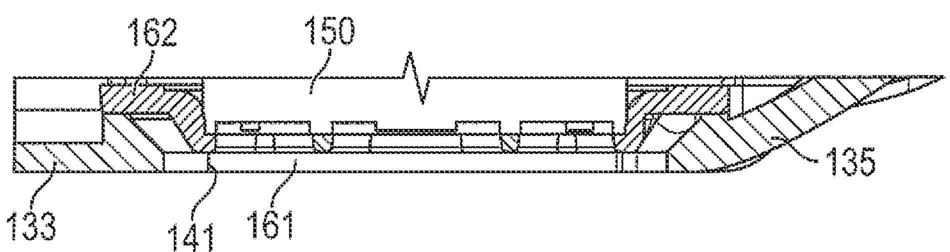
FIG. 11 is a side sectional view on the plethysmographic module assembled with the patient-facing surface of the exterior case of the insulin delivery pump of the alternative embodiment of FIG. 9.

Referring now to FIGS. 10 and 11, shell 133 of exterior case 111 is described, and includes an elongated concavity 142 having opening 141. Pins 143 are integrally molded with and project from the interior surface of shell 133 to facilitate locating and retention of photoplethysmographic package 150 centered over opening 141 in bump 135. Transparent window 161 is fixed in opening 141, e.g., using a biocompatible adhesive, heat bonding, or ultrasonic welding, beneath package 150 and silicone rubber retainer 160, to maintain a water-tight seal. When removably attached to an adhesive patch, the periphery of exterior case 111 adheres to the patch, while bump 135 extends through an opening in the adhesive patch. In accordance with one aspect of the invention, side walls 144 of bump 135 include gently sloping surfaces that reduce stretching of the skin in contact with bump 135. Initial testing of the design depicted in FIGS. 9-15 indicates that employing gently sloping sidewalls, together with a substantially elongated rectangular bump 135, reduces contact pressure necrosis and inflammation of the contacting skin, especially in diabetics who tend to have sensitive skin.

The design of photoplethysmography module 132 of FIGS. 9-15 differs from that of the previous embodiment in that bump 135 is integrally molded into shell 133 of exterior case 111, instead of being separately formed as frame 62 (see FIG. 6A) and attached to exterior case 11 (see FIG. 7). Preferably, the portion of the patient-facing side of exterior case 111 comprises a rigid plastic material, such as polyamide (nylon).

Figure 12:
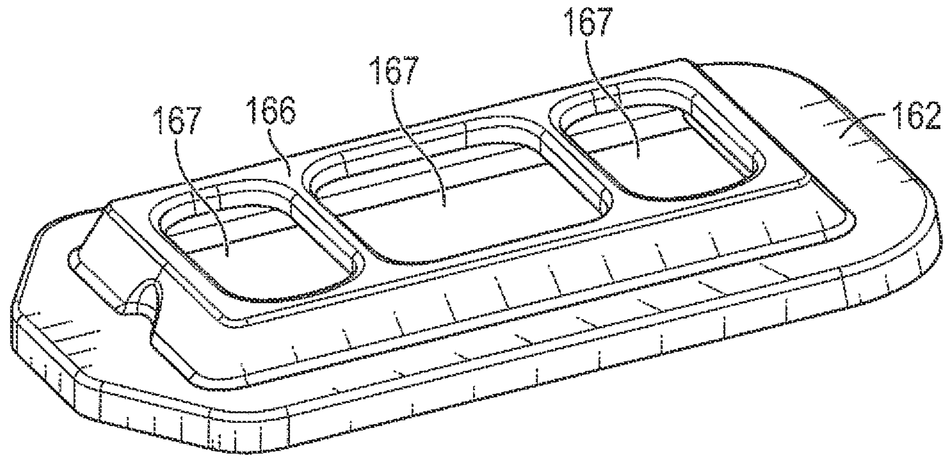
FIG. 12 is an enlarged perspective view of the silicone rubber retainer of FIG. 12 that retains the multi-chip package of the plethysmographic module in the alternative embodiment of FIG. 9.

Other differences with embodiment of FIGS. 1-8 include that transparent window 161 of the embodiment of FIGS. 9-15 is significantly thinner, preferable 0.3-0.4 mm in thickness, and that frame 62 and layer 60 of closed cell foam (see FIG. 6A) are replaced by a single component, frame 162 of FIG. 12. Referring now also to FIG. 12, frame 162 has raised indexed portion 166 having a thickness of about 0.2 mm, such that openings 167 in portion 166 align with light barriers 57 and 58 that separate compartments in photoplethysmographic package 50 to reduce optical crosstalk between the LEDs and detectors (see FIG. 5). The thicker periphery of frame 162 stabilizes the shape of the frame, which provides uniform spacing between the photoplethysmographic package 150 and window 161 without use of additional layer 60, as in the embodiment of FIGS. 1-8, as may be seen by comparing FIG. 11 to FIG. 12. In addition, the embodiment of FIGS. 9-15 eliminates layer 60 of the previous embodiment, reduces the thickness of frame 162 where it contacts photoplethysmographic package 150. By also configuring transparent window 161 as a planar sheet, the fields of view of the LED emitters and detectors of package 150 overlap to a greater extent compared to the prior embodiment, thereby ensuring a more robust plethysmographic signal. Plethysmographic package 150 used in this embodiment may be identical to package 50 used in the embodiment of FIGS. 1-8.

Figure 13:
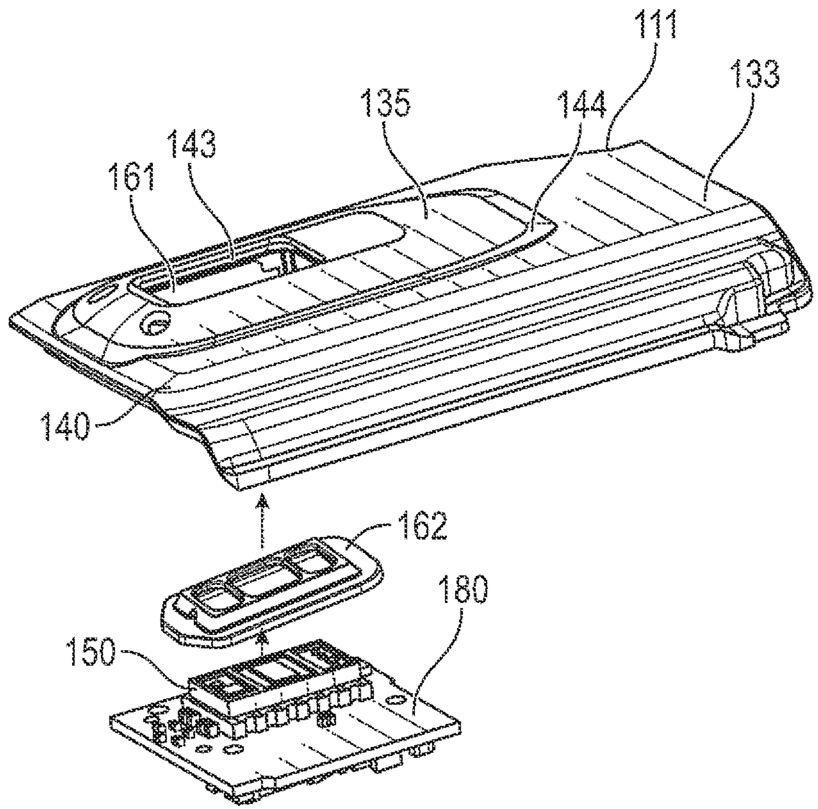
FIG. 13 is an exploded perspective view of the plethysmographic module of the alternative embodiment of FIG. 9.
Figure 14:
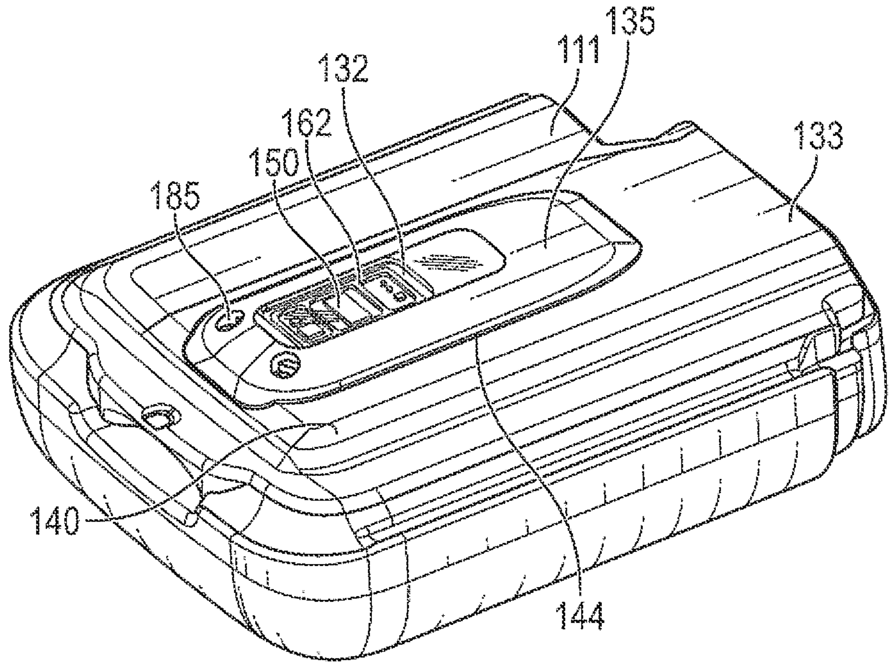
FIG. 14 is a perspective view of the patient-facing side of the pump case component of the alternative embodiment of present invention of FIG. 9.

Components of plethysmographic module 132 of the alternative embodiment are described with respect to FIGS. 13 and 14. In particular, FIG. 13 shows the plethysmographic package 150 mounted on printed circuit board 180, which is disposed in registration with openings 167 in frame 162. That assembly in turn is aligned so that package 150 is disposed beneath transparent window 161 disposed in opening 141 in bump 135 of shell 133 of exterior case 111. As described above, embossment 140 establishes a first plane above bump 35 extends so that when the patch pump is applied to a user's skin, bump 135 remains in continuous contact with a user's skin during motion. Bump 35 preferably protrudes above the surface of embossment 140 from about 0.6 mm to 2 mm, which height is selected to maintain contact of bump 35 with the user's skin. As described above, the edges of bump 35 are contoured as gently sloping surfaces to ensure that bump 35 does not apply excessive pressure to the skin that could cause stretching, inflammation or tissue necrosis.

Figure 15:
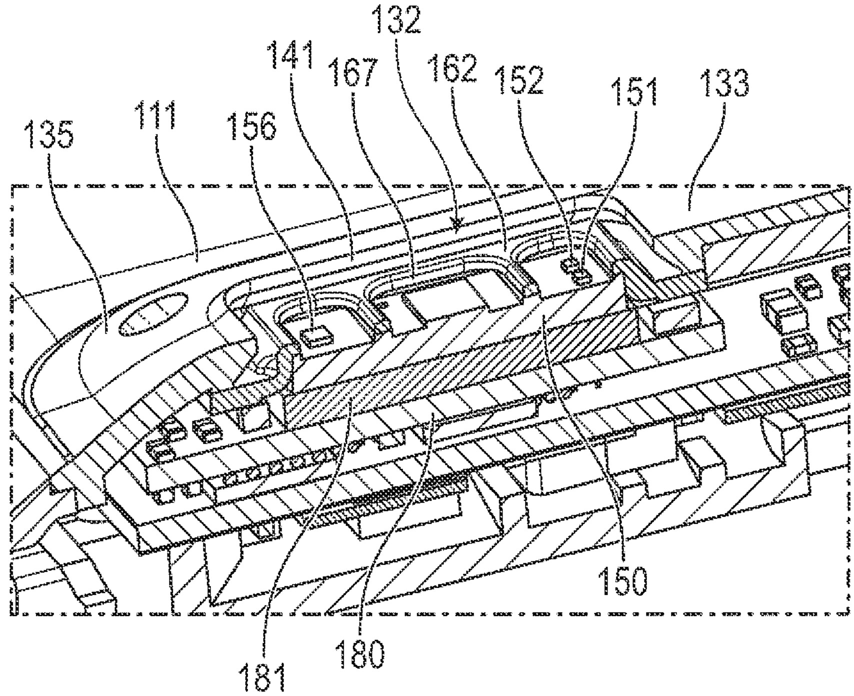
FIG. 15 is detailed perspective, cross-sectional, view of an assembled plethysmographic module (with glass window removed) of the embodiment of FIG. 9.

Referring now also to FIG. 15, components of plethysmographic module 132 of the alternative embodiment of the inventive patch pump, such as are visible in an enlarged sectional view of FIG. 14, are described. As depicted, photoplethysmographic package 150 may be mounted on printed circuit board 180 using spacer 181, such that red LED 151, infrared LED 152 and broadband detector 156 are aligned with openings 167 in frame 162. In this manner, light emitted from LEDs 151 and 152 is transmitted through transparent window 161 (not shown) and absorbed by the wearer's skin, and reflected light then is detected by detector 156. The positions of printed circuit board 180, frame 162, photoplethysmographic package 150 may be fixed relative to opening in bump 135 by pins 143 (see FIG. 10), and fasteners 185 that may be inserted recesses in shell 133. Printed circuit board 180 preferably is electrically coupled to the main circuit board of the patch pump controller, e.g., via a flex circuit, to provide signals that permit calculation of heart rate and/or blood oxygen saturation. Like the embodiment of FIGS. 1-8, circuit board 180 or the main circuit board additionally may have an accelerometer to determine the orientation of the user's body, e.g., upright or supine, to assess whether the user is active, resting or asleep.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A medication infusion device comprising:

a flexible adhesive patch configured to be removably attached to a wearer's skin, the flexible adhesive patch having a periphery that defines an opening;

a pump having a pump case with a lower surface configured to contact the periphery of the flexible adhesive patch, the lower surface including a bump configured to extend through the opening, the pump case configured to be removably coupled to the flexible adhesive patch to transcutaneously deliver doses of medication from a replaceable single-use cartridge disposed within the pump case to the wearer; and a photoplethysmographic module disposed within the bump, the photoplethysmographic module having an LED, a detector, and a skin contact element including at least one transparent window, wherein the LED emits light to, and the detector receives reflected light from, the wearer's skin through the at least one transparent window.

2. The medication infusion device of claim 1, wherein the bump protrudes from the pump case and is configured to urge the skin contact element into contact with the wearer's skin during motion.

3. The medication infusion device of claim 2, wherein the skin contact element is surrounded by a light-blocking rib.

4. The medication infusion device of claim 2, wherein the skin contact element has a substantially elongated rectangular shape and gently sloped sidewalls.

5. The medication infusion device of claim 1, wherein the patch pump further comprises a controller programmed to analyze signals output by the photoplethysmographic module to adjust an algorithm that controls delivery of medication to the wearer.

6. The medication infusion device of claim 5, wherein the controller is disposed on a main circuit board and the photoplethysmographic module is electrically coupled to the main circuit board by a flex circuit.

7. The medication infusion device of claim 5, further comprising an accelerometer disposed within the pump case and electrically coupled to the controller.

8. The medication infusion device of claim 1, wherein the pump further comprises a gear system and micro-dosing unit.

9. The medication infusion device of claim 8, wherein the micro-dosing unit includes cam-driven levers.

10. The medication infusion device of claim 1, wherein the LED and the detector are disposed on a ceramic package and the photoplethysmographic module further comprises a frame that retains the ceramic package at a uniform spacing from the at least one transparent window.

11. An insulin delivery device comprising:

an adhesive patch configured to be removably attached to a wearer's skin, the adhesive patch having a periphery that defines an opening;

a pump configured to be removably coupled to the adhesive patch to transcutaneously deliver insulin from an on-board replaceable single-use cartridge to the wearer, the pump having a pump case including a lower surface configured to adhere to the periphery of the adhesive patch, the lower surface including a protrusion that extends through the opening; and a plethysmographic module disposed within the protrusion, the plethysmographic module having an LED, a detector, and a skin contact element including at least one transparent window, wherein the LED emits light to, and the detector receives reflected light from, a skin surface of the wearer via the at least one transparent window.

12. The insulin delivery device of claim 11, wherein the protrusion is configured to retain the skin contact element of the plethysmographic module in contact with the skin surface during motion.

13. The insulin delivery device of claim 12, wherein the skin contact element is surrounded by a light-blocking rib.

14. The insulin delivery device of claim 12, wherein the protrusion has a substantially elongated rectangular shape and gently sloped sidewalls configured to reduce skin inflammation during prolonged contact.

15. The insulin delivery device of claim 11, wherein the pump further comprises a controller programmed to analyze signals output by the plethysmographic module to adjust an algorithm controlling delivery of insulin to the wearer.

16. The insulin delivery device of claim 15, wherein the controller is disposed on a main circuit board and the plethysmographic module is electrically coupled to the main circuit board by a flex circuit.

17. The insulin delivery device of claim 15, further comprising an accelerometer disposed within the pump case and electrically coupled to the controller.

18. The insulin delivery device of claim 11, wherein the pump further comprises a gear system and micro-dosing unit.

19. The insulin delivery device of claim 18, wherein the micro-dosing unit includes cam-driven levers.

20. The insulin delivery device of claim 11, wherein the LED and the detector are disposed on a ceramic package and the plethysmographic module further comprises a frame that retains the ceramic package at a uniform spacing from the at least one transparent window.

* * * * *